United States Patent
Brackenridge et al.

(12)

(10) Patent No.: US 6,359,146 B1
(45) Date of Patent: Mar. 19, 2002

(54) PROCESS FOR THE PRODUCTION OF R-(+)-6-CARBOXAMIDO-3-N-METHYLAMINO-1,2,3,4-TETRAHYDROCARBAZOLE

(75) Inventors: Ian Brackenridge; Caroline McGee, both of Abingdon (GB); Steven McIntyre, Basel (CH); John Knight, Oxon; David Hartley, Knebworth Hertfordshire, both of (GB)

(73) Assignee: Vernalis Limited, Berkshire (GB)

( * ) Notice: Subject to any disclaimer, the term of this patent is extended or adjusted under 35 U.S.C. 154(b) by 0 days.

(21) Appl. No.: 09/689,661

(22) Filed: Oct. 13, 2000

Related U.S. Application Data

(63) Continuation of application No. PCT/GB99/01167, filed on Apr. 16, 1999.

(30) Foreign Application Priority Data

Apr. 16, 1998 (GB) .............................................. 9808069

(51) Int. Cl.⁷ ............................................. C07D 209/84
(52) U.S. Cl. ....................................................... 548/439
(58) Field of Search ......................................... 548/439

(56) References Cited

U.S. PATENT DOCUMENTS

| | | | | |
|---|---|---|---|---|
| 2,528,267 A | * | 10/1950 | Dearborn et al. | 260/570.8 |
| 5,464,864 A | | 11/1995 | King et al. | 514/468 |
| 5,616,603 A | | 4/1997 | Borrett et al. | 514/411 |
| 5,618,947 A | | 4/1997 | Borrett et al. | 548/448 |
| 5,618,948 A | | 4/1997 | Borrett et al. | 548/448 |
| 5,637,611 A | | 6/1997 | King et al. | 514/468 |
| 5,650,426 A | | 7/1997 | Borrett et al. | 514/411 |
| 5,827,871 A | | 10/1998 | King et al. | 514/411 |
| 5,917,054 A | | 6/1999 | Borrett et al. | 548/448 |
| 5,962,501 A | | 10/1999 | Borrett et al. | 514/411 |

FOREIGN PATENT DOCUMENTS

| | | |
|---|---|---|
| EP | 0 204 481 A3 | 12/1986 |
| EP | 0 204 481 A2 | 12/1986 |
| WO | WO 93/00086 | 1/1993 |
| WO | WO 94/14772 | 7/1994 |

OTHER PUBLICATIONS

The Merck index, 18th edition.*
Tadashi, O., et al., "Optical resolution of DL–phenylalanine esters," *Chem. Abstracts* 78:556, Abstract No. 58800n, Chemical Abstracts Service (1973).

* cited by examiner

*Primary Examiner*—Floyd D. Higel
*Assistant Examiner*—Golam M. M. Shameem
(74) *Attorney, Agent, or Firm*—Sterne, Kessler, Goldstein & Fox, P.L.L.C.

(57) ABSTRACT

The present invention relates to a novel process for the preparation of R-(+)-6-carboxamido-3-N-methylamino-1,2,3,4-tetrahydrocarbazole. The process comprises resolving an enantiomeric mixture of a compound of formula (I):

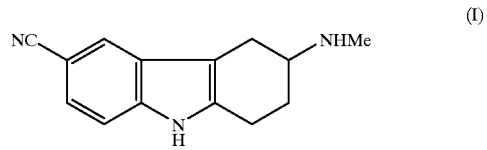

12 Claims, No Drawings

PROCESS FOR THE PRODUCTION OF R-(+)-6-CARBOXAMIDO-3-N-METHYLAMINO-1,2,3,4-TETRAHYDROCARBAZOLE

This is a continuation of International Application No. PCT/GB99/01167, with an International Filing Date of Apr. 16, 1999, the contents of which are fully incorporated by reference.

The present invention relates to a novel process for the preparation of R-(+)-6-carboxamido-3-N-methylamino-1,2,3,4-tetrahydrocarbazole.

WO-A-93/00086 describes a group of tetrahydrocarbazole derivatives, which have activity as $5HT_1$ receptor agonists and are therefore useful in the treatment of migraine. The specific compounds disclosed include inter alia 3-methylamino-6-carboxamido-1,2,3,4-tetrahydrocarbazole hydrochloride. WO-A-93/00086 also describes a preparation of 3-methylamino-6-carboxamido-1,2,3,4-tetrahydrocarbazole hydrochloride which comprises a six stage process, via 3-methylamino-6-cyano-1,2,3,4-tetrahydrocarbazole, involving a number of protection and deprotection steps.

WO-A-94/14772 describes enantiomers of certain carbazole derivatives, including the aforementioned compound. The enantiomers disclosed are:
R-(+)-6-carboxamido-3-N-methylamino-1,2,3,4-tetrahydrocarbazole;
S-(−)-6-carboxamido-3-N-methylamino-1,2,3,4-tetrahydrocarbazole;
R-(+)-6-carboxamido-3-N-ethylamino-1,2,3,4-tetrahydrocarbazole;
S-(−)-6-carboxamido-3-N-ethylamino-1,2,3,4-tetrahydrocarbazole;
and 3 salts and solvates thereof.

R-(+)-6-carboxamido-3-N-methylamino-1,2,3,4-tetrahydrocarbazole succinate has now entered clinical trials for the treatment of migraine.

WO-A-94/14772 provides various methods by which single enantiomers can be prepared, namely:
(i) separation of an enantiomeric mixture of the compound or a derivative thereof by chromatography, e.g. on a chiral HPLC column;
(ii) separation of diastereoisomers of a chiral derivative (e.g. a chiral salt) of the compound e.g. by crystallisation or chromatography; or
(iii) alkylation of (+) or (−) enantiomer of 3-amino-6-carboxamido-1,2,3,4-tetrahydrocarbazole or a salt thereof.

Although the above-noted procedures (i) to (iii) can be used to prepare the desired enantiomer, they are disadvantageous from the point of view of "scale-up" and the manufacture of commercial quantities of the compound. In particular it has been found that carrying out the resolution at the final stage of the synthesis and using R-2-pyrrolidone-5-carboxylic acid (also known as D-pyroglutamic acid) to form a chiral salt results in an intermediate with poor solubility and hence gives low yields of the desired enantiomer, despite the fact that R-2-pyrrolidone-5-carboxylic acid is described as a preferred optically active acid for use in the process described in WO-A-94/14772.

There is therefore a need to provide a more efficient method which more readily lends itself to commercial manufacture. We have now devised such a process for the preparation of R-(+)-6-carboxamido-3-N-methylamino-1,2,3,4-tetrahydrocarbazole. This process relies on resolution of an indole nitrile intermediate compound at a relatively early stage of the process. We have surprisingly found that this intermediate has good solubility and enables the desired enantiomer to be obtained in good yield. Indeed, although the new process has one more step than the process of WO-A-94/14772 it gives a greater overall yield of final product. Furthermore, carrying out the resolution on the nitrile intermediate ensures that subsequent steps are carried out on the correct enantiomeric form of intermediate compounds resulting in direct production of the compound without the need for chromatography or the like.

Thus, in a first aspect, the present invention provides a process for the preparation of R-(+)-6-carboxamido-3-N-methylamino-1,2,3,4-tetrahydrocarbazole which comprises the step of resolving a mixture of enantiomers of an indole nitrile compound of formula (I):

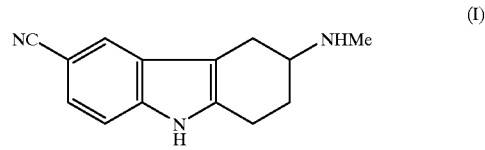

(I)

The compound of formula (I) may be named as 6-cyano-3-N-methylamino-1,2,3,4-tetrahydrocarbazole. It will be appreciated that the compound of formula (I) may comprise varying ratios of its two enantiomers. In particular it may exist as a racemic mixture.

It has been found that resolution of the mixture of indole nitrile enantiomers can advantageously be achieved by the use of L-pyroglutamic acid. Indeed, it was surprisingly found that use of D-pyroglutamic acid gave the 'wrong' enantiomer, whereas L-pyroglutamic acid gave the desired enantiomer in good yield. The use of L-pyroglutamic acid also has economic advantages as it is the naturally occurring form and hence considerably less expensive than the D-form. Reaction with the optically active acid to form a chiral salt may be effected in a suitable solvent, for example an alcohol such as methanol or ethanol and at a temperature in the range 0 to 100° C. The desired enantiomer is obtained by crystallisation using methods well known in the art. Crystallisation may be initiated spontaneously, or in some cases seeding may be required. The reaction mixture is desirably treated with acetic acid, preferably after crystallisation has been initiated. This has been found advantageously to facilitate selective crystallisation of the desired enantiomer. The resulting L-pyroglutamate salt may advantageously be recrystallised from aqueous methanol or more preferably aqueous ethanol to enhance the optical purity of the product. The chiral salt may be converted into the free base using standard procedures, to provide (+)-6-cyano-3-N-methylamino-1,2,3,4-tetrahydrocarbazole. If desired this compound may be directly reacted in situ to form the corresponding carboxamido compound.

(+)-6-Cyano-3-N-methylamino-1,2,3,4-tetrahydrocarbazole is a novel compound. Therefore, in a further aspect the present invention provides (+)-6-cyano-3-N-methylamino-1,2,3,4-tetrahydrocarbazole of formula (II):

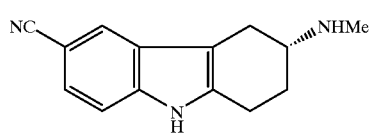

(II)

and salts and solvates thereof.

A preferred embodiment of this aspect of the invention is (+)-6-cyano-3-N-methylamino-1,2,3,4-tetrahydrocarbazole L-pyroglutamate.

The compound of formula (II) may be converted into the desired R-(+)-6-carboxamide-3-N-methylamino-1,2,3,4-tetrahydrocarbazole or a salt or solvate thereof.

In a further aspect therefore, the present invention provides a process for the preparation of R-(+)-6-carboxamido-3-N-methylamino-1,2,3,4-tetrahydrocarbazole or a salt or solvate thereof, which process comprises hydrolysing R-(+)-6-cyano-3-N-methylamino-1,2,3,4-tetrahydrocarbazole or a salt or solvate thereof. As will be readily apparent to those skilled in the art, a nitrile may be hydrolysed to give either an amide or a carboxylic acid, depending upon the conditions used. It will therefore be appreciated that in the present process the hydrolysis conditions should be chosen to give an amide rather than a carboxylic acid. Preferably hydrolysis is effected using acetic acid and boron trifluoride ($BF_3$)/acetic acid complex. Other means of hydrolysis which may be employed include hydrogen peroxide in the presence of an alkali hydroxide, such as sodium hydroxide, in a solvent such as an alcohol; or formic acid and hydrobromic or hydrochloric acid.

6-Cyano-3-N-methylamino-1,2,3,4-tetrahydrocarbazole employed as the starting material for the resolution step, may be prepared for example using the methods described in WO-A-93/00086. Alternatively, and more preferably 6-cyano-3-N-methylamino-1,2,3,4-tetrahydrocarbazole may be prepared by reacting 4-cyanophenyl hydrazine of formula (III):

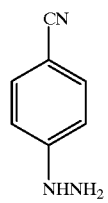

(III)

or a salt thereof e.g. the hydrochoride with 4-methylaminocyclohexanone or a protected derivative thereof. Advantageously the ketal derivative 4-methylaminocyclohexanone (2',2'-dimethyltrimethylene) ketal or a salt thereof, eg the hydrochloride, is employed:

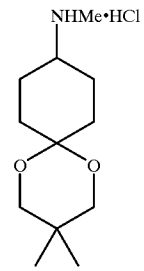

(IV)

The reaction is preferably effected under aqueous acidic conditions.

The aforementioned ketal derivative (IV) is a commercially available compound. It may be prepared for example by the method described in WO-A-94/14772, by reaction of the corresponding protected 1,4-cyclohexanedione of formula (V):

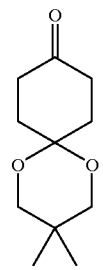

(V)

with methylamine.

The reaction is preferably effected in a suitable solvent, such as an alcohol, or a mixture thereof, e.g. industrial methylated spirits or methanol, with catalytic hydrogenation using for example palladium on charcoal.

A complete synthetic sequence from the keto-ketal of formula (V) to R-(+)-6-carboxamido-3-N-methylamino-1,2,3,4-tetrahydrocarbazole is as follows:

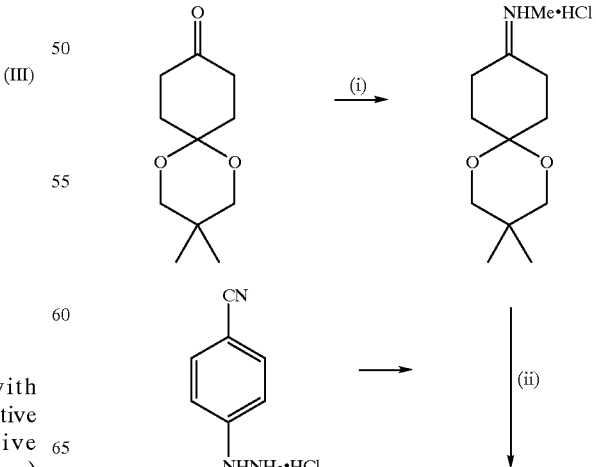

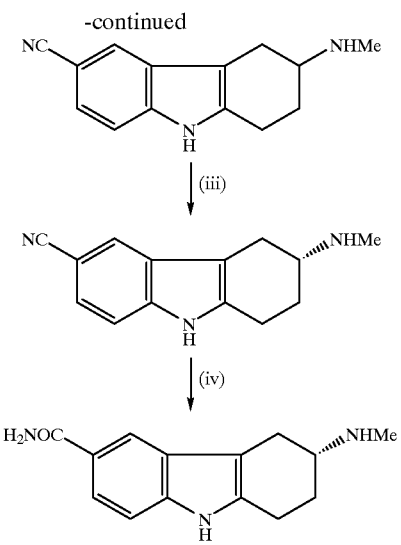

Preferred reaction conditions for the various steps are as follows:

(i) IMS, MeNH$_2$, H$_2$, Pd—C then THF, HCl, 0–10° C. e.g. 0–5° C. or preferably 5–10° C. (yield: 77–94% theory);

(ii) HCl(aq), 80–90° C. preferably 85–90° C. followed by 0–5° C. then NaOH(aq), THF followed by 0–5° C., (yield: 62–85% theory);

(iii) MeOH, L-pyroglutamic acid (L-PGA), AcOH, 50° C. or preferably reflux followed by 0–5° C. then recrystallization from aqueous MeOH or preferably EtOH, (yield: 14–30% theory);

(iv) AcOH, BF$_3$(AcOH)$_2$, 90–95° C. then NaOH, BuOH, then Na$_2$CO$_3$ or preferably water wash, (yield: 70–100% theory).

As an optional step (v) the resulting compound (II) from step (iv) can easily be converted to an appropriate salt form, e.g. a succinic acid salt by reaction with succinic acid in an alcohol such as ethanol or a mixture of alcohols such as ethanol and butanol. The reaction is preferably effected at a temperature in the range 60–100° C. eg 60–65° C. or preferably 70–100° C. then 20–25° C., (yield: 87–90% theory). The salt, eg the succinate may if desired or necessary be recrystallised, preferably using aqueous ethanol.

In a further embodiment therefore the present invention provides a process for the preparation of R-(+)-6-carboxamido-3-N-methylamino-1,2,3,4-tetrahydrocarbazole or a salt or solvate thereof, which comprises reaction steps (i) to (iv) above and optionally salt formation step (v).

As the amine ketal hydrochloride material used in step (ii) is a commercially available compound, the process can effectively consist of only steps (ii) to (iv).

In another aspect the present invention provides the use of L-pyroglutamic acid in resolving an enantiomeric mixture of an indole nitrile compound of the formula (I):

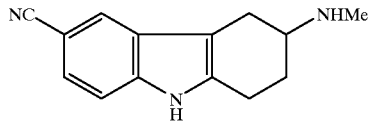

The present invention will now be described with reference to the following examples which should not be construed as in any way limiting the invention.

EXAMPLE 1

Resolution of a Racemic Mixture of 6-Cyano-3-N-methylamino-1,2,3,4-tetrahydrocarbazole (Indole Nitrile)

(a) Salt Formation

Racemic Indole Nitrile (1.72 mol, 387 g) was mixed with methanol (1.941) and the mixture stirred and heated to reflux to give a solution. Meanwhile, a second flask was charged with L-pyroglutamic acid (0.5 mol equiv., 110.9 g) and methanol (774 ml). The methanolic solution of the racemic Indole Nitrile was cooled to 50° C. and filtered directly into the L-pyroglutamic acid mixture followed by two rinses with methanol (774 ml and 387 ml). The water content of the resultant mixture was adjusted so as to fall within the range 0.7–2% w/v. The mixture was heated to reflux to give a solution and then cooled to 25° C., seeded and acetic acid (0.6 mol equiv., 59 ml) was added over 30 min at 25–28° C. The mixture was aged at 25° C. for 30 min and then cooled to 0–3° C. and aged for a further 2 h. The resulting solid was isolated by filtration and dried in vacuo at ambient temperature to give intermediate grade R-(+)-6-cyano-3-N-methylamino-1,2,3,4-tetrahydrocarbazole, Pyroglutamate salt (180.8 g).

(b) Recrystallisation

The intermediate grade Pyroglutamate salt (147.4 g) prepared in step (a) was mixed with water (120.6 ml) and 96% ethanol (363 ml) and the slurry was stirred and heated to reflux to give a solution. Further 96% ethanol (1.031) was added to the refluxing solution during 30 min and the mixture was then seeded. The mixture was cooled to 0–5° C. during 2 h and aged for a further 1–2 h. The solid was isolated by filtration and dried in vacuo at ambient temperature to give -R-(+)-6-cyano-3-N-methylamino-1,2,3,4-tetrahydrocarbazole, Pyroglutamate salt (123.2 g) with ee>98% by HPLC analysis.

EXAMPLE 2

Representative Preparation of R-(+)-6-carboxamido-3-N-methylamino-1,2,3,4-tetrahydrocarbazole succinate salt 2.1 Preparation of 4-methylaminocyclohexanone (2'2'-dimethyltrimethylene) Ketal Hydrochloride (Amine Ketal Hydrochoride)

Stage 1

The reaction vessel (RV2; nominal capacity 100 L; working capacity ca130 L) was charged with 5% palladium on charcoal (50% w/w paste, 1.25 kg) followed by 1,4-cyclohexanedione mono-2-(2',2'-dimethyltrimethylene) ketal (Keto Ketal) (125 kg). The reaction vessel was then purged with nitrogen before the addition of IMS (industrial methylated spirits; 75 L). The reaction was then stirred for 30 min until all the Keto Ketal dissolved. A solution of methylamine in ethanol (33% w/v, 2.6 mol equiv, 15.5 L) was then charged and the resultant mixture stirred under one atmosphere of hydrogen at 20 to 25° C. until the reaction was complete by gas chromatography (GC) (ca 12–14 h). The catalyst was filtered off by transfer via 1 μm filter to a second vessel (RV3; nominal capacity 250 L; working capacity ca300 L) followed by a line rinse with IMS (2×6.25 L) to the second vessel. The combined filtrate and washings were concentrated in vacuo at 35 to 40° C. to remove the IMS. The concentrate was held under nitrogen at <25° C. until a second portion of IMS solution was ready for transfer (see below).

In parallel with this concentration phase, a second Stage One reaction was started in RV2 on the same scale as that described above and once the reaction was complete (GC analysis as above), the reaction was filtered directly into RV3 and the concentrate from the first batch with the line rinses to follow. Again, the combined filtrate and washings were concentrated in vacuo at 35 to 40° C. to remove the IMS.

The residue was diluted with tetrahydrofuran (THF) (250 L) and the solution concentrated in vacuo at 35 to 40° C. to remove a portion (62.5 L) of the THF. The solution was made up once more with THF (62.5 L) and the concentration to remove 62.5 L was repeated. The solution was then cooled to 0 to 5° C. and treated with concentrated hydrochloric acid (1.2 mol equiv, 12.5 L) at such a rate as to maintain the temperature below 10° C. throughout. The resultant mixture was cooled to 0 to 5° C. and aged for 1 to 2 h. The solid was collected by filtration on a 27" nutsche filter, washed by displacement with THF (2×25 L) and dried in vacuo at 40° C. to constant weight (typically overnight) to give the Amine Ketal Hydrocloride as a white solid (26.92 kg corrected for solvent content, 85.5% th, 107.7% w/w).

2.2 Preparation of 6-Cyano-3-N-methylamino-1,2,3,4-tetrahydrocarbazole (Racemic Indole Nitrile)

4-Cyanophenylhydrazine hydrochloride (26.24 kg) and the Amine Ketal hydrochloride (1 mol equiv. 38.57 kg) were charged to the reaction vessel (RV3; nominal capacity 250 L; working capacity ca300 L) followed by water (92 L) and conc. hydrochloric acid (65.6 L). The reaction mixture was stirred and heated to 80–90° for up to ca 5 h and monitored by proton NMR (see note below). When the reaction was deemed to be complete, the reaction mixture was cooled to 0–5° C. and aged for 1 hour at this temperature. The racemic Indole Nitrile Hydrochloride was filtered using a 27" nutsche filter and washed thoroughly with water (3×26 L or until the washing is >pH5). The damp racemic Indole Nitrile Hydrochloride was then charged back into RV3, followed by water (164.5 L) and THF (66 L). The pH was adjusted to pH 13 with 6M NaOH (ca 30 L) and the reaction mixture stirred for 30 min. A sample was removed, the solid filtered off and checked by proton NMR (see note be low) to ensure the free base had been generated. The THF was then distilled off in vacuo at <40° C., the aqueous reaction mixture cooled to 0–5° C. and aged for a further 1 h. The solid was isolated by filtration using a 27" nutsche filter, washed by displacement with water (2×33 L or until the washings are <pH9) and dried in vacuo at 55–60° C. to constant weight to give the racemic Indole Nitrile as an off-white solid (25.13 kg corrected for water content, 72.2% th, 65%w/w vs the Hydrazine hydrochloride input).

Note: NMR IPC Methods
Determination of End-point of the Reaction

A sample of the reaction mixture is removed from the vessel and filtered under vacuum. Approximately 20 mg of the solid is dissolved in 1–2 ml of $D_6$-DMSO and the NMR spectrum is collected using a 360 MHz NMR spectrometer. The spectrum is examined for disappearance of the signals relating to the Hydrazine hydrochloride at δ7.05 ppm (2H, doublet) and δ7.7 ppm (2H, doublet). The distinctive signals in the aromatic region relating to the racemic Indole Nitrile Hydrochloride intermediate are at δ7.9 ppm (1H, singlet) and δ7.3–7.5 (2H, multiplet).

Confirmation of Free Base Formation

A sample of the reaction mixture is removed from the vessel and filtered under vacuum. Approximately 20 mg of the solid is dissolved in 1–2 ml of $D_6$-DMSO and the NMR spectrum is collected using a 360 MHz NMR spectrometer. The signal for the N-methyl group in the racemic Indole nitrile hydrochloride moves from its starting shift of δ2.65 ppm (singlet) to the shift of δ2.38 ppm (singlet) for the free base, the racemic Indole nitrile. It is important that the shift of δ2.38 ppm is obtained since mixtures of the hydrochloride and free base will exhibit N-methyl shifts within this range due to equilibration in the NMR solution.

2.3 Preparation of R-(+)-6-cyano-3-N-methylamino-1,2,3,4-tetrahydrocarbazole Pyroglutamate The racemic Indole Nitrile (1 mol equiv, 25.13 kg) and L-pyroglutamic acid (0.5 mol equiv. 7.3 kg) were charged to the reaction vessel (RV3; nominal capacity 250 L; working capacity ca300 L) followed by methanol (250 L) and the stirred mixture was heated to reflux to give a solution. The mixture was cooled to 50° C. and acetic acid (0.6 mol equiv. 3.8 L) added over approximately 15 min. The solution was seeded after the acetic acid addition, aged at 50–55° C. for 30 min, and stirred whilst cooling to 0–5° C. at a constant rate over 2 h. The slurry was aged at this temperature for 2 h. The solid was filtered using a 27" nutsche filter and washed with methanol (1×25 L, 1×12.5 L). The resulting solid was either dried in vacuo at room temperature to constant weight (typical output; 47–50%w/w of ca 94%ee material) or used methanol-wet in the recrystallisation having corrected for methanol content by proton NMR.

Recrystallisation of the Salt to Meet Optical Specification

The solid (24.11 kg) was charged to the reaction vessel (RV3; nominal capacity 250 L; working capacity ca300 L) followed by methanol (206 L) and water (21.7 L). The mixture was heated to reflux and stirred until all the solid dissolved (typically 30 min). The mixture was cooled to 55–60° C., seed crystals introduced and the mixture aged at 55–60° C. for 30 min, then cooled to 0–5° C. at constant rate during 1 h and aged for 2 h. The resulting solid was filtered using a 27" nutsche filter, washed by displacement with methanol (24 L), and dried in vacuo at room temperature to constant weight. The Pyroglutamate was isolated as an off-white to white solid (16.81 kg corrected for methanol and water content, 69.7% w/w). The product has essentially the same IR and NMR spectra as the product of Example 3.2.

2.4 Preparation of R-(+)-6-carboxamido-3-N-methylamino-1,2,3,4-tetrahydrocarbazole The reaction vessel (RV2, nominal capacity 100 L; working capacity ca130 L) was charged with the Pyroglutamate salt (1 mol equiv. 22.0 kg), acetic acid (55 L) and demineralised water (5 mol equiv, 5.5 L) to give a dark brown solution on stirring. Boron trifluoride-acetic acid complex (6 mol equiv, 52.8 L) was added in one portion and a thick, white precipitate formed. The stirred mixture was heated at 90–95° and the precipitate redissolved as the temperature reaches 95° C. to give a dark brown solution. The reaction was monitored by HPLC analysis for disappearance of the Pyroglutamate and formation of R-(+)-6-carboxamido-3-N-methylamino-1,2,3,4-tetrahydrocarbazole and Indole carboxylic acid (as a by-product). When the reaction was complete (typically ca5–8 h reaction time), the mixture was cooled to 25–30° and added to stirred cooled (0–4° C.) water (110 L) in RV3 (nominal capacity 250 L; working capacity up to ca300 L) over 10 min maintaining the temperature below 30° throughout (some fuming may occur at this point). n-Butanol (110 L) was added and the mixture cooled to 5–10° C. The pH was adjusted to 7 and the contents transferred to a stainless steel vessel (MV1, nominal capacity 600 L: working capacity ca650 L) and the pH further adjusted 12–14 by the addition of 6M sodium hydroxide solution over ca 1 h maintaining the temperature below 30° C. throughout (ca 330 L is required to give pH13). The layers are allowed to settle and then separated. The aqueous layer was further extracted with n-butanol (1×110 L, 1×55 L). The combined organic extract was washed with ca 10%w/v sodium carbonate solution (2×44 L). The carbonate washes were combined and back-extracted with n-butanol (44 L). All the organic extracts were combined in RV3 and concentrated in vacuo to ca 130 L maintaining an internal temperature below 50° C. throughout. The concentrate was treated with base-washed charcoal (pH range 6–8, 1.1 kg) added as slurry in n-butanol (22 L) and the stirred mixture was heated and stirred at reflux for 15 min. The mixture was cooled to 40–45° C., clarified in portions through a 1 µm filter into the distillate receiver of RV3 (i.e. DR3; capacity 100 L) followed by a line rinse of 96% ethanol (8.8 L). The solution of R-(+)-6-carboxamido-3-N-methylamino-1,2,3,4-tetrahydrocarbazole was transferred as necessary to a previously unused drum and a sample was removed for HPLC analysis to determine the product content (11.6 kg, 77.2% th, 52.7%w/w). The solution of R-(+)-6-carboxamido-3-N-methylamino-1,2,3,4-tetrahydrocarbazole was taken directly on to the next stage for the formation of the succinate salt.

2.5 Preparation of R-(+)-6-carboxamido-3-N-methylamino-1,2,3,4-tetrahydrocarbazole, Succinate Salt The reaction vessel (RV3, nominal capacity 250 L; working capacity 300 L) was charged with ethanol (98.5 L), demineralised water (23.2 L) and succinic acid (1 mol equiv, 5.68 kg) and the mixture heated to 70° with stirring until all the succinic acid dissolved (ca30 min). A solution of R-(+)-6-carboxamido-3-N-methylamino-1,2,3,4-tetrahydrocarbazole (contained weight; 11.59 kg) in n-butanol/ethanol solution (total solution weight: 143 kg) was added over 30 minutes, maintaining the internal temperature at 60–65° throughout, with a line rinse of warm (ca40° C.) n-butanol/ethanol mixture (2:1, 17.4 L). At the midpoint of the addition, the mixture was seeded with R-(+)-6-carboxamido-3-N-methylamino-1,2,3,4-tetrahydrocarbazole (succinate salt) (the product may crystallise out of solution during the addition of the butanol solution to the succinic acid solution. In this case seeding is not necessary; when the addition is complete the stirred mixture is heated to reflux for ca 20 min then cooled as described hereafter. Ageing at 55–60° C. is unnecessary).

When the addition was complete, the hot mixture was cooled to 55–60° C. and aged for 1 h. The mixture was further cooled to 25° C. over a 2 h period, at a rate of 5° C. every 20 min followed by stirring the suspension at 25° C. for 12–15 h. The solid was filtered using a 27" nutsche filter and washed by displacement with cooled (5° C.) 96% ethanol (2×8.7 L). The wet-cake was dried in vacuo at ambient temperature for up to 30 h to give the product R-(+)-6-carboxamido-3-N-methylamino-1,2,3,4-tetrahydrocarbazole succinate salt monohydrate as an off-white solid (15.52 kg, 85.9%th, 133.9%w/w). The product has essentially the same IR and NMR spectra as the product of Example 3.5.

EXAMPLE 3

Representative Preparation of R-(+)-6 carboxamido-3-N-methylamino-1,2,3,4-tetrahydrocarbazole succinate 3.1 Preparation of R-(+)-6-cyano-3-N-methylamino-1,2,3,4-tetrahydrocarbazole pyroglutamate Racemic Indole nitrile (1 mol equiv, 21.57 Kg) was charged to the 100 L reaction vessel (working capacity ca130 L), followed by methanol (105 L). The mixture was stirred at 60–65° C. until all the racemic Indole Nitrile had dissolved (1 hr 31 min). L-Pyroglutamic acid (0.5 mol equiv, 6.26 Kg) was charged to the 250 L reaction vessel (working capacity ca300 L), followed by methanol (43.5 L). The solution of racemic Indole nitrile was cooled to 50–55° C., clarified through a 1 µm filter and transferred into the 250 L vessel. This was followed by two line rinses of methanol (43.5 L, then 21 L), each of which were heated to 50–55° C. before transfer. The contents of the 250 L vessel were sampled to determine the water content of the mixture and further demineralised water was added to give a mixture containing 0.79%w/v (limits 0.7–2.0%w/v). The stirred mixture in the 250 L vessel was heated to reflux to obtain a full solution. The mixture was cooled to 24–26° C. and, if necessary, seeded to initiate crystallisation. Acetic acid (0.6 mol equiv, 3.48 Kg) was added, maintaining the internal temperature at 23–28° C., with the addition taking 18 min. The mixture was aged at 20–25° C. for 35 min, cooled to 10–12° C. over 40 min, further cooled to 5° C. and stirred at 0–5° C. for 2 hr 55 min. The material was filtered off and washed with methanol (1×21 L, 1×11 L). The resulting solid was dried in vacuo at a temperature up to 45° C. (10.95 Kg (corrected) of 93.2%de material, 50.8%w/w). Alternatively, the solid could have been used methanol-wet in the recrystallisation, being corrected for methanol content by proton NMR.

3.2 Recrystallisation of R-(+)-6-cyano-3-N-methylamino-1,2,3,4-tetrahydro-carbazole pyroglutamate The crude Pyroglutamate (21.73 Kg), 96% ethanol (53 L) and demineralised water (11.9 L) were charged to the 250 L reaction vessel (working capacity ca300 L). The mixture was stirred and heated to reflux. As there was not complete dissolution, further demineralised water (1.7 L, max. limit 2.8 L) was added. 96% Ethanol (152 L) was then added to the solution, maintaining the temperature above 75° C. The solution was then seeded, if necessary, and aged at 70–75° C. for 15 min. The mixture was cooled to 10–12° C. over 80 min, further cooled to 0–5° C. and aged at this temperature for 1 hr 55 min. The resulting solid was filtered off, washed with 96% ethanol (2×22 L) and dried in vacuo at a temperature up to 45° C. to constant weight. The Pyroglutamate was obtained as an off-white to white solid (17.89 Kg corrected for solvent and water content, 26.5%th, 41.8%w/w vs the Racemic Indole Nitrile input).

The product is identified by the following characteristics:

Infra-red spectrum: The product was prepared as a potassium bromide disc at a nominal concentration of 1% and the IR spectrum measured between 4000 and 500 cm$^{-1}$ at 21° C. on a Mattson 2020 Galaxy FTIR instrument, giving the following major peaks: ν(cm$^{-1}$) 3222; 3055–2440 (NH$_2^+$); 2216 (—CN); 1688 (—C═O); 1643 (—C═O); 1563 (N—H bending); 1481 (aromatic C—H vibrations); 1464 (C—H deformations CH$_2$ and CH$_3$); 1275, 1228 (—C—O stretching); 805 (C—H out of plane deformation).

Proton ($^1$H) NMR: The proton ($^1$H) NMR 270 MHz spectrum of the product was obtained in deuterated DMSO, giving the following main peaks: δ(ppm) 11.5 (NH, indole); 7.9 (aromatic H); 7.47 (NH pyroglutamate); 7.43 (aromatic H); 7.34 (aromatic H); 3.9 (pyroglutamate); 3.7 (water); 3.2, 3.15, 2.85 and 2.7 (tetrahydrocarbazole); 2.55 (CH$_3$); 2.5 (DMSO); 2.2 (pyroglutamate and tetrahydrocarbazole); 2.1 (pyroglutamate); 1.9 (pyroglutamate; and tetrahydrocarbazole).

3.3 Preparation of R-(+)-6-carboxamido-3-N-methylamino-1,2,3,4-tetrahydro-carbazole The 100 L reaction vessel (working capacity ca130 L) was charged with the Pyroglutamate salt (1 mol equiv, 5.93 Kg), acetic acid (9 L) and demineralised water (5 mol equiv, 1.48 L) to give a dark brown solution on stirring. Boron trifluoride-acetic acid complex (6 mol equiv, 14.1 L) was added in one portion, followed by acetic acid line rinses (2×3 L) and a thick, white precipitate was formed. The stirred mixture was heated at 90–95° C. and the precipitate dissolved (as the temperature reached 95° C.) to give a dark brown solution. The reaction was monitored by HPLC analysis for disappearance of the Pyroglutamate salt and formation of R-(+)-6-carboxamido-3-N-methylamino-1,2,3,4-tetrahydrocarbazole and Indole carboxylic acid (by-product). When the reaction was complete (6 hr 18 min), the mixture was cooled to 25–30° C. and added to stirred, cool (5–10° C.) demineralised water (31 L) in the 250 L reaction vessel (working capacity ca300 L), maintaining the temperature below 30° C. throughout, the addition taking 12 min. This was followed by a line rinse of demineralised water (5 L). n-Butanol (29 L) was added and the mixture was cooled to 5–10° C. The pH was adjusted to 14 by the addition of ca 6M sodium hydroxide solution (106 L), maintaining the temperature below 30° C. throughout, the addition taking 61 min. The temperature was adjusted to 25–30° C. and the phases were allowed to settle and then separated. The aqueous phase was further extracted with n-butanol (1×29 L, 1×15 L) at 25–30° C. throughout. The combined organic extracts were washed with demineralised water (5×12 L) at 25–30° C. throughout. The organic solution was concentrated in vacuo to 37 L, maintaining an internal temperature of 40–50° C. throughout. The concentrate was treated with a charcoal (60 g) slurry in n-butanol (6 L) and the stirred mixture was heated at reflux for 27 min. The mixture was cooled to 55–60° C., clarified through a 1 μm filter, followed by a line rinse of 96% ethanol (11.5 L) at 55–60° C. and a sample was removed for HPLC analysis to determine the product content (3.76 Kg, 92.4%th, 63.4%w/w). The solution of R-(+)-6-carboxamido-3-N-methylamino-1,2,3,4-tetrahydrocarbazole was taken directly on to the next stage for the formation of the succinate salt.

3.4 Preparation of R-(+)-6-carboxamido-3-N-methylamino-1,2,3,4-tetrahydro-carbazole succinate salt A solution of R-(+)-6-carboxamido-3-N-methylamino-1,2,3 4-tetrahydrocarbazole in n-butanol/ethanol solution (1 mol equiv, 8.77 Kg in 114 L) in the 100 L reaction vessel (working capacity ca130 L) was concentrated in vacuo to 42 L, maintaining an internal temperature of 70–100° C., followed by temperature adjustment to 65–70° C. 96% Ethanol (11.5 L) was added, maintaining, the internal temperature at 65–70° C., giving a solution of R-(+)-6-carboxamido-3-N-methylamino-1,2,3,4-tetrahydrocarbazole in 3.82:1 n-butanol:ethanol solution (limits 3–4:1). As solid was present, the mixture was heated to 85–90° C. and stirred at this temperature to obtain a full solution before cooling to 65–70° C. In the 250 L reaction vessel succinic acid (1.1 mol equiv, 4.65 Kg) was dissolved in ethanol/water (3:1, 88 L) and heated to 48–50° C. A check was made that no precipitation had occurred at this point. The solution of R-(+)-6-carboxamido-3-N-methylamino-1,2,3,4-tetrahydrocarbazole (at 65–70° C.) was clarified through a 1 μm into the succinic acid solution at 48–50° C. in the 250 L reaction vessel, this addition taking 60 min, followed by a line rinse of 96% ethanol (9 L), also at 65–70° C. At this point, all material was in solution. The mixture was cooled to 24–26° C. over 60 min and, if necessary, seeded. n-Butanol (88 L) was adjusted to 20–25° C. and added to the crystallisation mixture, over 30 min, maintaining the temperature of the mixture at 20–25° C. The mixture was cooled to 8–10° C. over 80 min. The mixture was further cooled to −2° C. to 2° C., followed by stirring at this temperature for a further 1 hr 40 min. The solid was collected by filtration, washed by displacement with 96% ethanol (2×9 L) and dried in vacuo at a temperature up to 25° C. to give R-(+)-6-carboxamido-3-N-methylamino-1,2,3,4-tetrahydrocarbazole succinate salt monohydrate a white to off-white solid (12.23 Kg (corrected), 89.4%th, 139.4% w/w).

3.5 Recrystallisation of R-(+)-6-carboxamido-3-N-methylamino-1,2,3,4-tetrahydrocarbazole succinate salt monohydrate R-(+)-6-carboxamido-3-N-methylamino-1,2,3,4-tetrahydrocarbazole succinate salt monohydrate (11.66 Kg), demineralised water (29.08 L) and 96% ethanol (80 L) were charged to the 100 L reaction vessel (working capacity ca130 L) and the mixture was heated to 40° C. to effect full dissolution. The solution was clarified through a 1 μm filter into the 250 L reaction vessel (working capacity ca 300 L), followed by a line rinse of 96% ethanol (30 L), also at 40° C. The stirred mixture was heated to reflux over 1 hr 20 min, during which time full dissolution occurred. The mixture may be held at reflux for up to 1 hr to ensure full dissolution as necessary. The solution was then cooled to 0–10° C. over 2 hr 53 min, during which time the product started to crystallise out of solution to give a viscous slurry. The mixture was further cooled to 0–5° C., followed by stirring at this temperature for a further 1 hr 53 min. The solid was collected by filtration, washed by displacement with 96% ethanol (1×22.5 L) and dried in vacuo at a temperature up to 25° C. to give R-(+)-6-carboxamido-3-N-methylamino-1,2,3,4-tetrahydrocarbazole succinate salt monohydrate as a white to off-white solid (8.72 Kg (corrected), 74.8% w/w). The product is identified by the following characteristics:

Infra-red spectrum: The product was prepared as a potassium bromide disc at a nominal concentration of 1% and the IR spectrum measured between 4000 and 500 $cm^{-1}$ at 21° C. on a Mattson 2020 Galaxy FTIR instrument, giving the following major peaks: ν($cm^{-1}$) 3500–2000 (Water OH, broad); 3399 (N—H stretch); 3180 (aromatic C—H stretch); 2930, 2842 (aliphatic C—H stretch); 2484 (N—H stretch); 1668 (—C=O stretch); 1627 (—C=C stretch); 1585, 1568 and 1475 (aromatic C=C skeletal stretch); 1410 (O—H bending); 1261, 1111 (—C—N stretch); 888, 812 (aromatic ring C—H).

Proton ($^1$H) NMR: The proton ($^1$H) NMR 500 MHz spectrum of the product was obtained in deuterated DMSO, giving the following main peaks: δ (ppm): 11.1 (cyclic NH); 8.05 (aromatic H); 7.85 (one H of $NH_2$); 7.65, 7.3 (aromatic H); 7.05 (one H of $NH_2$); 6.7 (very broad, COOH, N$\underline{H}$$CH_3$ and $H_2O$); 3.35, 3.15, 2.85 and 2.7 (tetrahydrocarbazole); 2.65 ($CH_3$); 2.5 (DMSO); 2.33 (succinate); 2.25, 1.9 (tetrahydrocarbazole).

What is claimed is:

1. A process for the preparation of R-(+)-6-carboxamido-3-N-methylamino-1,2,3,4-tetrahydrocarbazole which comprises the step of resolving an enantiomeric mixture of a compound of formula (I):

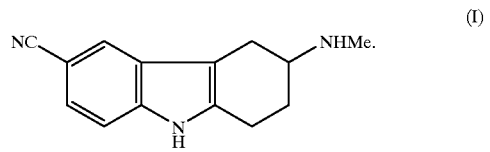

2. The process as claimed in claim 1 wherein resolution of the enantiomers is achieved by treating the mixture with L-pyroglutamic acid.

3. The process as claimed in claim 1 wherein the compound of formula (I) comprises a racemic mixture of enantiomers.

4. A process for the preparation of R-(+)-6-carboxamido-3-N-methylamino-1,2,3,4-tetrahydrocarbazole or a salt or solvate thereof which comprises hydrolysis of R-(+)-6-cyano-3-N-methylamino-1,2,3,4-tetrahydrocarbazole or a salt or solvate thereof optionally followed by salt formation.

5. The process as claimed in claim 1 for the preparation of R-(+)-6-carboxamido-3-N-methylamino-1,2,3,4-tetrahydrocarbazole or a salt or solvate thereof which comprises:

(a) resolving an enantiomeric mixture of 6-cyano-3-N-methylamino-1,2,3,4-tetrahydrocarbazole to give R-(+)-6-cyano-3-N-methylamino-1,2,3,4-tetrahydrocarbazole or a salt or solvate thereof, and (b) hydrolysis of R-(+)-6-cyano-3-N-methylamino-1,2,3,4-tetrahydrocarbazole or a salt or solvate thereof; optionally followed by salt formation.

6. The process as claimed in claim 1 wherein 6-cyano-3-N-methylamino-1,2,3,4-tetrahydrocarbazole of formula (I) is prepared by reacting 4-cyanophenyl hydrazine with 4-methylaminocyclohexanone or a protected derivative thereof.

7. The process according to claim 6 wherein the protected derivative of 4-methylaminocyclohexanone is 4-methylaminocyclohexanone (2',2'-dimethyltrimethylene) ketal hydrochloride.

8. The process according to claim 7 wherein 4-methylaminocyclohexanone (2',2'-dimethyltrimethylene) ketal hydrochloride is prepared by reacting (1,4-cyclohexanedione mono-2,2-dimethyltrimethylene ketal with methylamine.

9. The process as claimed in claim 1 wherein the process comprises steps (i) to (iv) as described herein, optionally followed by salt formation.

10. A compound of the formula II:

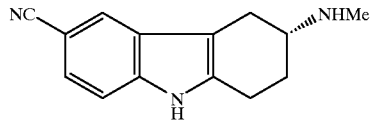

or a salt or solvate thereof.

11. R-(+)-6-cyano-3-N-methylamino-1,2,3,4-tetrahydrocarbazole L-pyroglutamate.

12. A method of resolving an enantiomeric mixture of a compound of formula (I):

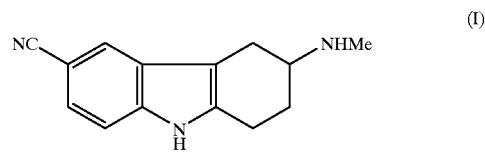

wherein the method comprises treating the enantiomeric mixture with L-pyroglutamic acid.

* * * * *